United States Patent
Schäfer et al.

[11] Patent Number: 6,010,980
[45] Date of Patent: Jan. 4, 2000

[54] SUBSTITUTED 2-PHENYLPYRIDINES AS HERBICIDES

[75] Inventors: Peter Schäfer, Ottersheim; Gerhard Hamprecht, Weinheim; Elisabeth Heistracher, Mannheim; Olaf Menke, Altleiningen; Cyrill Zagar, Ludwigshafen; Michael Rack, Heidelberg; Norbert Götz, Worms; Albrecht Harreus, Ludwigshafen; Karl-Otto Westphalen, Speyer; Helmut Walter, Obrigheim; Ulf Misslitz, Neustadt, all of Germany

[73] Assignee: BASF Aktiengesellschaft, Ludwigshafen, Germany

[21] Appl. No.: 09/029,994
[22] PCT Filed: Sep. 9, 1996
[86] PCT No.: PCT/EP96/03949
§ 371 Date: Mar. 13, 1998
§ 102(e) Date: Mar. 13, 1998
[87] PCT Pub. No.: WO97/11059
PCT Pub. Date: Mar. 27, 1997

[30] Foreign Application Priority Data

Sep. 18, 1995 [DE] Germany .......................... 195 34 466

[51] Int. Cl.[7] .......................... A01N 43/40; C07D 213/61
[52] U.S. Cl. .......................... 504/244; 546/330; 546/334; 546/335; 546/337; 546/342; 546/345; 546/346
[58] Field of Search .................... 546/342, 345, 546/346, 330, 334, 335, 337; 504/244

[56] References Cited

FOREIGN PATENT DOCUMENTS

| | | |
|---|---|---|
| 95/02580 | 1/1995 | WIPO . |
| 95/02590 | 1/1995 | WIPO . |
| 96/21645 | 7/1996 | WIPO . |
| 96/21646 | 7/1996 | WIPO . |
| 96/21647 | 7/1996 | WIPO . |

Primary Examiner—Evelyn Mei Huang
Attorney, Agent, or Firm—Keil & Weinkauf

[57] ABSTRACT

Substituted 2-phenylpyridines I and their salts

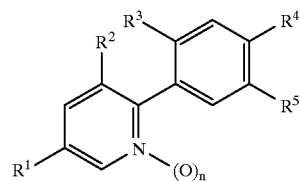

where
n=0, 1;
$R^1$=halogen, $C_1$–$C_4$-haloalkyl;
$R^2$ and $R^3$=H, halogen;
$R^4$=CN, halogen;
$R^5$=—CO—O-($C_1$–$C_4$-alkylene)-CO—$OR^6$, —CO—O-($C_1$–$C_4$-alkylene)-CO—N($R^7$)$R^8$, —O-($C_1$–$C_4$-alkylene)-CO—O-($C_1$–$C_4$-alkylene)-CO—$OR^6$, —O-($C_1$–$C_4$-alkylene)-CO—O-($C_1$–$C_4$-alkylene)-CO—N($R^7$)$R^8$, —S-($C_1$–$C_4$-alkylene)-CO—O-($C_1$–$C_4$-alkylene)-CO—$OR^6$ or —S-($C_1$–$C_4$-alkylene)-CO—O-($C_1$–$C_4$-alkylene)-CO—N($R^7$)$R^8$;
$R^6$=H, $C_1$–$C_4$-alkyl, $C_1$–$C_4$-alkoxy-$C_1$–$C_4$-alkyl, $C_2$–$C_4$-alkenyl, $C_3$–$C_4$-alkynyl;
$R^7$=H, $C_1$–$C_4$-alkyl, carboxy-$C_1$–$C_4$-alkyl, $C_1$–$C_4$-alkoxycarbonyl-$C_1$–$C_4$-alkyl;
$R^8$=H or $C_1$–$C_4$-alkyl,
are used as herbicides and for the desiccation/defoliation of plants.

15 Claims, No Drawings

SUBSTITUTED 2-PHENYLPYRIDINES AS HERBICIDES

This application is the national phase of PCT/EP 96/03949, filed Sep. 9, 1996, published as WO 97/11059 on Mar. 3, 1997.

The present invention relates to novel substituted 2-phenylpyridines of the formula I

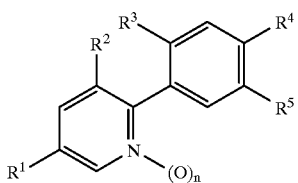

where the variables have the following meanings:
n is 0 or 1;
$R^1$ is halogen or $C_1$–$C_4$-haloalkyl;
$R^2$ and $R^3$ are in each case hydrogen or halogen;
$R^4$ is cyano or halogen;
$R^5$ is —CO—O-($C_1$–$C_4$-alkylene)-CO—$OR^6$, —CO—O-($C_1$–$C_4$-alkylene)-CO—N($R^7$) $R_8$, —O-($C_1$–$C_4$-alkylene)-CO—O-($C_1$–$C_4$-alkylene)-CO—$OR^6$, —O-($C_1$–$C_4$-alkylene)-CO—O-($C_1$–$C_4$-alkylene)-CO—N($R^7$)$R^8$, —S-($C_1$–$C_4$-alkylene)-CO—O-($C_1$–$C_4$-alkylene)-CO—$OR^6$ or —S-($C_1$–$C_4$-alkylene)-CO—O-($C_1$–$C_4$-alkylene)-CO—N($R^7$)$R_8$, where
$R^6$ is hydrogen, $C_1$–$C_4$-alkyl, $C_1$–$C_4$-alkoxy-$C_1$–$C_4$-alkyl, $C_2$–$C_4$-alkenyl or $C_3$–$C_4$-alkynyl,
$R^7$ is hydrogen, $C_1$–$C_4$-alkyl, carboxy-$C_1$–$C_4$-alkyl, ($C_1$–$C_4$-alkoxy)carbonyl-$C_1$–$C_4$-alkyl and
$R^8$ is hydrogen or $C_1$–$C_4$-alkyl,
and to the agriculturally useful salts of the compounds I where $R^6$=hydrogen.

The invention furthermore relates to
the use of the compounds I as herbicides or for the desiccation and/or defoliation of plants,
herbicidal compositions and compositions for the desiccation and/or defoliation of plants which comprise the compounds I as active ingredients,
methods of controlling undesirable vegetation and for the desiccation and/or defoliation of plants using the compounds I,
processes for the preparation of the compounds I and herbicidal compositions and compositions for the desiccation and/or defoliation of plants using the compounds I, and
intermediates of the formula IIb and a process for their preparation.

Herbicidally active substituted 2-phenylpyridines have already been disclosed in WO 95/02580, WO 95/02590 and the earlier German Applications DE-A 19 500 760, DE-A 19 500 758, DE-A 19 500 911 and DE-A 19 528 943.

WO 95/02580 describes a multiplicity of herbicidally active 2-phenylpyridines. However, this publication does not describe the compounds of the formula I and their especially advantageous properties.

Regarding the harmful plants, the herbicidal action of the known compounds is, however, not always fully satisfactory.

It is an object of the present invention to provide novel herbicidally active compounds which allow better targeted control of undesirable plants than has been possible to date. It is also an object of the present invention to provide novel compounds which act as desiccants/defoliants.

We have found that these objects are achieved by the herbicidally active substituted 2-phenylpyridines of the formula I defined at the outset, and by novel intermediates IIb for their preparation.

We have also found herbicidal compositions which comprise the compounds I and which have very good herbicidal action. We have furthermore found processes for the preparation of these compositions and methods of controlling undesirable vegetation using the compounds I.

We have furthermore found that the compounds I are also suitable for the defoliation/desiccation of parts of plants, suitable crop plants being cotton, potatoes, oil seed rape, sunflowers, soya beans or field beans, in particular cotton and potatoes. Thus, we have found compositions for the desiccation and/or defoliation of plants, processes for the preparation of these compositions and methods for the desiccation and/or defoliation of plants using the compounds I.

Depending on their substitution pattern, the compounds of the formula I can contain one or more chiral centers, in which case they are present as enantiomer or diastereomer mixtures. The invention relates to the pure enantiomers or diastereomers and to their mixtures.

The substituted 2-phenylpyridines I where $R^6$=hydrogen can be present in the form of their agriculturally useful salts, the nature of the salt generally not being important. Suitable salts are generally salts of those bases where the herbicidal action is not adversely affected in comparison with the free compound I.

Especially useful salts are salts of the alkali metals, preferably sodium and potassium salts, of the alkaline earth metals, preferably calcium and magnesium salts, of the transition metals, preferably zinc and iron salts, and ammonium salts where the ammonium ion can have attached to it, if desired, one to four $C_1$–$C_4$-alkyl, hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl(2-hydroxyethyl)ammonium salts, furthermore phosphonium salts, sulfonium salts such as preferably tri($C_1$–$C_4$-alkyl)sulfonium salts, and sulfoxonium salts such as preferably tri($C_1$–$C_4$-alkyl)sulfoxonium salts.

The terms alkyl, haloalkyl, alkoxy, carboxyalkyl, alkoxyalkyl, alkoxycarbonylalkyl, alkenyl and alkynyl—and the term halogen—which are used in the definition of the substituents $R^1$, $R^6$, $R^7$ and $R^8$ are collective terms for individual enumerations of the individual group members. All alkyl moieties can be straight-chain or branched. The haloalkyl radical preferably has attached to it one to five identical or different halogen atoms.

Examples of individual meanings are:
halogen: fluorine, chlorine, bromine or iodine;
$C_1$–$C_4$-alkyl: methyl, ethyl, n-propyl, 1-methylethyl, n-butyl, 1-methylpropyl, 2-methylpropyl or 1,1-dimethylethyl;
$C_1$–$C_4$-haloalkyl: a $C_1$–$C_4$-alkyl radical as mentioned above which is partially or fully substituted by fluorine, chlorine, bromine and/or iodine, eg. $CH_2Cl$, dichloromethyl, trichloromethyl, $CH_2F$, $CHF_2$, $CF_3$, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_4$-alkoxy: $OCH_3$, $OC_2H_5$, n-propoxy, $OCH(CH_3)_2$, n-butoxy, 1-methylpropoxy, 2-methylpropoxy or 1,1-dimethylethoxy;

$C_1$–$C_4$-alkoxy-$C_1$–$C_4$-alkyl: $C_1$–$C_4$-alkyl which is substituted by $C_1$–$C_4$-alkoxy, such as methoxy, ethoxy, n-propoxy, 1-methylethoxy, n-butoxy, 1-methylpropoxy, 2-methylpropoxy and 1,1-dimethylethoxy, eg. $CH_2OCH_3$, $CH_2OC_2H_5$, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably $CH_2OCH_3$, $CH_2OC_2H_5$, 2-methoxyethyl or 2-ethoxyethyl;

($C_1$–$C_4$-alkoxy)carbonyl-$C_1$–$C_4$-alkyl: $C_1$–$C_4$-alkyl which is substituted by ($C_1$–$C_4$-alkoxy)carbonyl, such as $COOCH_3$, $COOC_2H_5$, n-propoxycarbonyl, $COOCH(CH_3)_2$, n-butoxycarbonyl, 1-methylpropoxycarbonyl, 2-methylpropoxycarbonyl and $COOC(CH_3)_3$, eg. $CH_2$—$COOCH_3$, $CH_2$—$COOC_2H_5$, n-propoxycarbonylmethyl, $CH_2$—$COOCH(CH_3)_2$, n-butoxycarbonylmethyl, (1-methylpropoxycarbonyl)methyl, (2-methylpropoxycarbonyl)methyl, $CH_2$—$COOC(CH_3)_3$, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(n-propoxycarbonyl)propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl, 4-(1-methylpropoxycarbonyl)butyl, 4-(2-methylpropoxycarbonyl)butyl or 4-(1,1-dimethylethoxycarbonyl)butyl, preferably $CH_2$—$COOCH_3$, $CH_2$—$COOC_2H_5$, 1-(methoxycarbonyl)ethyl or 1-(ethoxycarbonyl)ethyl;

carboxy-$C_1$–$C_4$-alkyl: carboxymethyl, 1-carboxyethyl, 2-carboxyethyl, 1-carboxyprop-1-yl, 2-carboxyprop-1-yl, 3-carboxyprop-1-yl, 1-carboxybut-1-yl, 2-carboxybut-1-yl, 3-carboxybut-1-yl, 4-carboxybut-1-yl, 1-carboxybut-2-yl, 2-carboxybut-2-yl, 3-carboxybut-2-yl, 3-carboxybut-2-yl, 4-carboxybut-2-yl, 1-(carboxymethyl)eth-1-yl, 1-(carboxymethyl)-1-(methyl)eth-1-yl or 1-(carboxymethyl)prop-1-yl, preferably carboxymethyl or 1-carboxyethyl;

$C_2$–$C_4$-alkenyl: vinyl, prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl and 2-methylprop-2-en-1-yl, preferably allyl or 2-buten-1-yl;

$C_3$–/$C_4$-alkynyl: prop-1-yn-1-yl, prop-2-yn-1-yl, n-but-1-yn-1-yl, n-but-1-yn-3-yl, n-but-1-yn-4-yl or n-but-2-yn-1-yl, preferably prop-2-yn-1-yl.

$C_1$–$C_4$-Alkylene is, for example, methylene, 1,1-ethylene, 1,2-ethylene, 1,1-propylene, 1,2-propylene, 1,3-propylene, 2,2-propylene, 1,1-butylene, 1,2-butylene, 1,3-butylene, 1,4-butylene, 2,2-butylene, 2,3-butylene, 2-methyl-1,1-propylene, 2-methyl-1,2-propylene or 2-methyl-1,3-propylene, preferably ethylene, 1,1-ethylene or 2,2-propylene.

Regarding the use of the substituted 2-phenylpyridines I according to the invention as herbicides and/or as compounds which act as desiccants/defoliants, the variables preferably have the following meanings, in each case alone or in combination:

n is zero;

$R^1$ is chlorine or trifluoromethyl;

$R^2$ is chlorine;

$R^3$ is hydrogen, fluorine or chlorine;

$R^4$ is cyano or chlorine;

$R^5$ is —CO—O-($C_1$–$C_4$-alkylene)-CO—$OR^6$, —CO—O-($C_1$–$C_4$-alkylene)-CO—N($R^7$)$R^8$, —O-($C_1$–$C_4$-alkylene)-CO—O-($C_1$–$C_4$-alkylene)-CO—$OR^6$ or —O-($C_1$–$C_4$-alkylene)-CO—O-($C_1$–$C_4$-alkylene)-CO—N($R^7$)$R^8$, where $R^6$ is $C_1$–$C_4$-alkyl, $C_2$–$C_4$-alkenyl or $C_3$–$C_4$-alkynyl, $R^7$ is $C_1$–$C_4$-alkyl or ($C_1$–$C_4$-alkoxy)carbonyl-$C_1$–$C_4$-alkyl and $R^8$ is hydrogen or $C_1$–$C_4$-alkyl.

Especially preferred are the substituted 2-phenylpyridines Ia (=I where n=zero, $R^2$ and $R^4$=chlorine), in particular the compounds listed in Table 1 below:

TABLE 1

(Ia)

| No. | R¹ | R³ | R⁵ | M.p. [° C.] |
|---|---|---|---|---|
| Ia. 01 | CF$_3$ | H | —CO—OCH$_2$—CO—OCH$_3$ | |
| Ia. 02 | Cl | H | —CO—OCH$_2$—CO—OCH$_3$ | |
| Ia. 03 | CF$_3$ | F | —CO—OCH$_2$—CO—OCH$_3$ | oil |
| Ia. 04 | Cl | F | —CO—OCH$_2$—CO—OCH$_3$ | |
| Ia. 05 | CF$_3$ | Cl | —CO—OCH$_2$—CO—OCH$_3$ | |
| Ia. 06 | Cl | Cl | —CO—OCH$_2$—CO—OCH$_3$ | |
| Ia. 07 | CF$_3$ | H | —CO—OCH$_2$—CO—OC$_2$H$_5$ | |
| Ia. 08 | Cl | H | —CO—OCH$_2$—CO—OC$_2$H$_5$ | |
| Ia. 09 | CF$_3$ | F | —CO—OCH$_2$—CO—OC$_2$H$_5$ | 68 (Ex. 1) |
| Ia. 10 | Cl | F | —CO—OCH$_2$—CO—OC$_2$H$_5$ | |
| Ia. 11 | CF$_3$ | Cl | —CO—OCH$_2$—CO—OC$_2$H$_5$ | |
| Ia. 12 | Cl | Cl | —CO—OCH$_2$—CO—OC$_2$H$_5$ | |
| Ia. 13 | CF$_3$ | H | —CO—OCH(CH$_3$)—CO—OCH$_3$ | |
| Ia. 14 | Cl | H | —CO—OCH(CH$_3$)—CO—OCH$_3$ | |
| Ia. 15 | CF$_3$ | F | —CO—OCH(CH$_3$)—CO—OCH$_3$ | Example 2 |
| Ia. 16 | Cl | F | —CO—OCH(CH$_3$)—CO—OCH$_3$ | |
| Ia. 17 | CF$_3$ | Cl | —CO—OCH(CH$_3$)—CO—OCH$_3$ | |
| Ia. 18 | Cl | Cl | —CO—OCH(CH$_3$)—CO—OCH$_3$ | |
| Ia. 19 | CF$_3$ | H | —CO—OCH(CH$_3$)—CO—OC$_2$H$_5$ | |
| Ia. 20 | Cl | H | —CO—OCH(CH$_3$)—CO—OC$_2$H$_5$ | |
| Ia. 21 | CF$_3$ | F | —CO—OCH(CH$_3$)—CO—OC$_2$H$_5$ | oil |
| Ia. 22 | Cl | F | —CO—OCH(CH$_3$)—CO—OC$_2$H$_5$ | |
| Ia. 23 | CF$_3$ | Cl | —CO—OCH(CH$_3$)—CO—OC$_2$H$_5$ | |
| Ia. 24 | Cl | Cl | —CO—OCH(CH$_3$)—CO—OC$_2$H$_5$ | |
| Ia. 25 | CF$_3$ | H | —CO—OCH$_2$—CO—N(CH$_3$)$_2$ | |
| Ia. 26 | Cl | H | —CO—OCH$_2$—CO—N(CH$_3$)$_2$ | |
| Ia. 27 | CF$_3$ | F | —CO—OCH$_2$—CO—N(CH$_3$)$_2$ | |
| Ia. 28 | Cl | F | —CO—OCH$_2$—CO—N(CH$_3$)$_2$ | |
| Ia. 29 | CF$_3$ | Cl | —CO—OCH$_2$—CO—N(CH$_3$)$_2$ | |
| Ia. 30 | Cl | Cl | —CO—OCH$_2$—CO—N(CH$_3$)$_2$ | |
| Ia. 31 | CF$_3$ | H | —CO—OCH(CH$_3$)—CO—N(CH$_3$)$_2$ | |
| Ia. 32 | Cl | H | —CO—OCH(CH$_3$)—CO—N(CH$_3$)$_2$ | |
| Ia. 33 | CF$_3$ | F | —CO—OCH(CH$_3$)—CO—N(CH$_3$)$_2$ | |
| Ia. 34 | Cl | F | —CO—OCH(CH$_3$)—CO—N(CH$_3$)$_2$ | |
| Ia. 35 | CF$_3$ | Cl | —CO—OCH(CH$_3$)—CO—N(CH$_3$)$_2$ | |
| Ia. 36 | Cl | Cl | —CO—OCH(CH$_3$)—CO—N(CH$_3$)$_2$ | |
| Ia. 37 | CF$_3$ | H | —OCH$_2$—CO—OCH$_2$—CO—OCH$_3$ | |
| Ia. 38 | Cl | H | —OCH$_2$—CO—OCH$_2$—CO—OCH$_3$ | |
| Ia. 39 | CF$_3$ | F | —OCH$_2$—CO—OCH$_2$—CO—OCH$_3$ | 95–96 |
| Ia. 40 | Cl | F | —OCH$_2$—CO—OCH$_2$—CO—OCH$_3$ | |
| Ia. 41 | CF$_3$ | Cl | —OCH$_2$—CO—OCH$_2$—CO—OCH$_3$ | |
| Ia. 42 | Cl | Cl | —OCH$_2$—CO—OCH$_2$—CO—OCH$_3$ | |
| Ia. 43 | CF$_3$ | H | —OCH$_2$—CO—OCH$_2$—CO—OC$_2$H$_5$ | |
| Ia. 44 | Cl | H | —OCH$_2$—CO—OCH$_2$—CO—OC$_2$H$_5$ | |
| Ia. 45 | CF$_3$ | F | —OCH$_2$—CO—OCH$_2$—CO—OC$_2$H$_5$ | 102–103 |
| Ia. 46 | Cl | F | —OCH$_2$—CO—OCH$_2$—CO—OC$_2$H$_5$ | |
| Ia. 47 | CF$_3$ | Cl | —OCH$_2$—CO—OCH$_2$—CO—OC$_2$H$_5$ | |
| Ia. 48 | Cl | Cl | —OCH$_2$—CO—OCH$_2$—CO—OC$_2$H$_5$ | |
| Ia. 49 | CF$_3$ | H | —OCH$_2$—CO—OCH(CH$_3$)—CO—OCH$_3$ | |
| Ia. 50 | Cl | H | —OCH$_2$—CO—OCH(CH$_3$)—CO—OCH$_3$ | |
| Ia. 51 | CF$_3$ | F | —OCH$_2$—CO—OCH(CH$_3$)—CO—OCH$_3$ | 83–84 |
| Ia. 52 | Cl | F | —OCH$_2$—CO—OCH(CH$_3$)—CO—OCH$_3$ | |
| Ia. 53 | CF$_3$ | Cl | —OCH$_2$—CO—OCH(CH$_3$)—CO—OCH$_3$ | |
| Ia. 54 | Cl | Cl | —OCH$_2$—CO—OCH(CH$_3$)—CO—OCH$_3$ | |
| Ia. 55 | CF$_3$ | H | —OCH$_2$—CO—OCH(CH$_3$)—CO—OC$_2$H$_5$ | |
| Ia. 56 | Cl | H | —OCH$_2$—CO—OCH(CH$_3$)—CO—OC$_2$H$_5$ | |
| Ia. 57 | CF$_3$ | F | —OCH$_2$—CO—OCH(CH$_3$)—CO—OC$_2$H$_5$ | 106–107 |
| Ia. 58 | Cl | F | —OCH$_2$—CO—OCH(CH$_3$)—CO—OC$_2$H$_5$ | |
| Ia. 59 | CF$_3$ | Cl | —OCH$_2$—CO—OCH(CH$_3$)—CO—OC$_2$H$_5$ | |
| Ia. 60 | Cl | Cl | —OCH$_2$—CO—OCH(CH$_3$)—CO—OC$_2$H$_5$ | |
| Ia. 61 | CF$_3$ | H | —OCH(CH$_3$)—CO—OCH$_2$—CO—OCH$_3$ | |
| Ia. 62 | Cl | H | —OCH(CH$_3$)—CO—OCH$_2$—CO—OCH$_3$ | |
| Ia. 63 | CF$_3$ | F | —OCH(CH$_3$)—CO—OCH$_2$—CO—OCH$_3$ | oil |
| Ia. 64 | Cl | F | —OCH(CH$_3$)—CO—OCH$_2$—CO—OCH$_3$ | |
| Ia. 65 | CF$_3$ | Cl | —OCH(CH$_3$)—CO—OCH$_2$—CO—OCH$_3$ | |

TABLE 1-continued

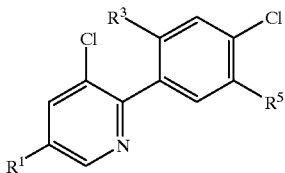
(Ia)

| No. | R¹ | R³ | R⁵ | M.p. [° C.] |
|---|---|---|---|---|
| Ia. 66 | Cl | Cl | —OCH(CH₃)—CO—OCH₂—CO—OCH₃ | |
| Ia. 67 | CF₃ | H | —OCH(CH₃)—CO—OCH₂—CO—OC₂H₅ | |
| Ia. 68 | Cl | H | —OCH(CH₃)—CO—OCH₂—CO—OC₂H₅ | |
| Ia. 69 | CF₃ | F | —OCH(CH₃)—CO—OCH₂—CO—OC₂H₅ | oil |
| Ia. 70 | Cl | F | —OCH(CH₃)—CO—OCH₂—CO—OC₂H₅ | |
| Ia. 71 | CF₃ | Cl | —OCH(CH₃)—CO—OCH₂—CO—OC₂H₅ | |
| Ia. 72 | Cl | Cl | —OCH(CH₃)—CO—OCH₂—CO—OC₂H₅ | |
| Ia. 73 | CF₃ | H | —OCH(CH₃)—CO—OCH(CH₃)—CO—OCH₃ | |
| Ia. 74 | Cl | H | —OCH(CH₃)—CO—OCH(CH₃)—CO—OCH₃ | |
| Ia. 75 | CF₃ | F | —OCH(CH₃)—CO—OCH(CH₃)—CO—OCH₃ | oil |
| Ia. 76 | Cl | F | —OCH(CH₃)—CO—OCH(CH₃)—CO—OCH₃ | |
| Ia. 77 | CF₃ | Cl | —OCH(CH₃)—CO—OCH(CH₃)—CO—OCH₃ | |
| Ia. 78 | Cl | Cl | —OCH(CH₃)—CO—OCH(CH₃)—CO—OCH₃ | |
| Ia. 79 | CF₃ | H | —OCH(CH₃)—CO—OCH(CH₃)—CO—OC₂H₅ | |
| Ia. 80 | Cl | H | —OCH(CH₃)—CO—OCH(CH₃)—CO—OC₂H₅ | |
| Ia. 81 | CF₃ | F | —OCH(CH₃)—CO—OCH(CH₃)—CO—OC₂H₅ | oil |
| Ia. 82 | Cl | F | —OCH(CH₃)—CO—OCH(CH₃)—CO—OC₂H₅ | |
| Ia. 83 | CF₃ | Cl | —OCH(CH₃)—CO—OCH(CH₃)—CO—OC₂H₅ | |
| Ia. 84 | Cl | Cl | —OCH(CH₃)—CO—OCH(CH₃)—CO—OC₂H₅ | |
| Ia. 85 | CF₃ | H | —OCH₂—CO—OCH₂—CO—N(CH₃)₂ | |
| Ia. 86 | Cl | H | —OCH₂—CO—OCH₂—CO—N(CH₃)₂ | |
| Ia. 87 | CF₃ | F | —OCH₂—CO—OCH₂—CO—N(CH₃)₂ | |
| Ia. 88 | Cl | F | —OCH₂—CO—OCH₂—CO—N(CH₃)₂ | |
| Ia. 89 | CF₃ | Cl | —OCH₂—CO—OCH₂—CO—N(CH₃)₂ | |
| Ia. 90 | Cl | Cl | —OCH₂—CO—OCH₂—CO—N(CH₃)₂ | |
| Ia. 91 | CF₃ | H | —OCH₂—CO—OCH(CH₃)—CO—N(CH₃)₂ | |
| Ia. 92 | Cl | H | —OCH₂—CO—OCH(CH₃)—CO—N(CH₃)₂ | |
| Ia. 93 | CF₃ | F | —OCH₂—CO—OCH(CH₃)—CO—N(CH₃)₂ | |
| Ia. 94 | Cl | F | —OCH₂—CO—OCH(CH₃)—CO—N(CH₃)₂ | |
| Ia. 95 | CF₃ | Cl | —OCH₂—CO—OCH(CH₃)—CO—N(CH₃)₂ | |
| Ia. 96 | Cl | Cl | —OCH₂—CO—OCH(CH₃)—CO—N(CH₃)₂ | |
| Ia. 97 | CF₃ | H | —OCH(CH₃)—CO—OCH₂—CO—N(CH₃)₂ | |
| Ia. 98 | Cl | H | —OCH(CH₃)—CO—OCH₂—CO—N(CH₃)₂ | |
| Ia. 99 | CF₃ | F | —OCH(CH₃)—CO—OCH₂—CO—N(CH₃)₂ | |
| Ia. 10 | Cl | F | —OCH(CH₃)—CO—OCH₂—CO—N(CH₃)₂ | |
| Ia. 101 | CF₃ | Cl | —OCH(CH₃)—CO—OCH₂—CO—N(CH₃)₂ | |
| Ia. 102 | Cl | Cl | —OCH(CH₃)—CO—OCH₂—CO—N(CH₃)₂ | |
| Ia. 103 | CF₃ | H | —OCH(CH₃)—CO—OCH(CH₃)—CO—N(CH₃)₂ | |
| Ia. 104 | Cl | H | —OCH(CH₃)—CO—OCH(CH₃)—CO—N(CH₃)₂ | |
| Ia. 105 | CF₃ | F | —OCH(CH₃)—CO—OCH(CH₃)—CO—N(CH₃)₂ | |
| Ia. 106 | Cl | F | —OCH(CH₃)—CO—OCH(CH₃)—CO—N(CH₃)₂ | |
| Ia. 107 | CF₃ | Cl | —OCH(CH₃)—CO—OCH(CH₃)—CO—N(CH₃)₂ | |
| Ia. 108 | Cl | Cl | —OCH(CH₃)—CO—OCH(CH₃)—CO—N(CH₃)₂ | |
| Ia. 109 | CF₃ | H | —SCH₂—CO—OCH₂—CO—OCH₃ | |
| Ia. 110 | Cl | H | —SCH₂—CO—OCH₂—CO—OCH₃ | |
| Ia. 111 | CF₃ | F | —SCH₂—CO—OCH₂—CO—OCH₃ | oil |
| Ia. 112 | Cl | F | —SCH₂—CO—OCH₂—CO—OCH₃ | |
| Ia. 113 | CF₃ | Cl | —SCH₂—CO—OCH₂—CO—OCH₃ | |
| Ia. 114 | Cl | Cl | —SCH₂—CO—OCH₂—CO—OCH₃ | |
| Ia. 115 | CF₃ | H | —SCH₂—CO—OCH₂—CO—OC₂H₅ | |
| Ia. 116 | Cl | H | —SCH₂—CO—OCH₂—CO—OC₂H₅ | |
| Ia. 117 | CF₃ | F | —SCH₂—CO—OCH₂—CO—OC₂H₅ | |
| Ia. 118 | Cl | F | —SCH₂—CO—OCH₂—CO—OC₂H₅ | |
| Ia. 119 | CF₃ | Cl | —SCH₂—CO—OCH₂—CO—OC₂H₅ | |
| Ia. 120 | Cl | Cl | —SCH₂—CO—OCH₂—CO—OC₂H₅ | |
| Ia. 121 | CF₃ | H | —SCH₂—CO—OCH(CH₃)—CO—OCH₃ | |
| Ia. 122 | Cl | H | —SCH₂—CO—OCH(CH₃)—CO—OCH₃ | |
| Ia. 123 | CF₃ | F | —SCH₂—CO—OCH(CH₃)—CO—OCH₃ | |
| Ia. 124 | Cl | F | —SCH₂—CO—OCH(CH₃)—CO—OCH₃ | |
| Ia. 125 | CF₃ | Cl | —SCH₂—CO—OCH(CH₃)—CO—OCH₃ | |
| Ia. 126 | Cl | Cl | —SCH₂—CO—OCH(CH₃)—CO—OCH₃ | |
| Ia. 127 | CF₃ | H | —SCH₂—CO—OCH(CH₃)—CO—OC₂H₅ | |
| Ia. 128 | Cl | H | —SCH₂—CO—OCH(CH₃)—CO—OC₂H₅ | |
| Ia. 129 | CF₃ | F | —SCH₂—CO—OCH(CH₃)—CO—OC₂H₅ | |
| Ia. 130 | Cl | F | —SCH₂—CO—OCH(CH₃)—CO—OC₂H₅ | |
| Ia. 131 | CF₃ | Cl | —SCH₂—CO—OCH(CH₃)—CO—OC₂H₅ | |

TABLE 1-continued

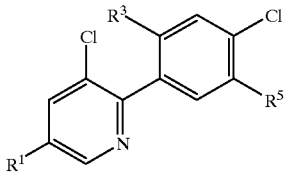

(Ia)

| No. | R¹ | R³ | R⁵ | M.p. [° C.] |
|---|---|---|---|---|
| Ia. 132 | Cl | Cl | —SCH₂—CO—OCH(CH₃)—CO—OC₂H₅ | |
| Ia. 133 | CF₃ | H | —SCH(CH₃)—CO—OCH₂—CO—OCH₃ | |
| Ia. 134 | Cl | H | —SCH(CH₃)—CO—OCH₂—CO—OCH₃ | |
| Ia. 135 | CF₃ | F | —SCH(CH₃)—CO—OCH₂—CO—OCH₃ | |
| Ia. 136 | Cl | F | —SCH(CH₃)—CO—OCH₂—CO—OCH₃ | |
| Ia. 137 | CF₃ | Cl | —SCH(CH₃)—CO—OCH₂—CO—OCH₃ | |
| Ia. 138 | Cl | Cl | —SCH(CH₃)—CO—OCH₂—CO—OCH₃ | |
| Ia. 139 | CF₃ | H | —SCH(CH₃)—CO—OCH₂—CO—OC₂H₅ | |
| Ia. 140 | Cl | H | —SCH(CH₃)—CO—OCH₂—CO—OC₂H₅ | |
| Ia. 141 | CF₃ | F | —SCH(CH₃)—CO—OCH₂—CO—OC₂H₅ | |
| Ia. 142 | Cl | F | —SCH(CH₃)—CO—OCH₂—CO—OC₂H₅ | |
| Ia. 143 | CF₃ | Cl | —SCH(CH₃)—CO—OCH₂—CO—OC₂H₅ | |
| Ia. 144 | Cl | Cl | —SCH(CH₃)—CO—OCH₂—CO—OC₂H₅ | |
| Ia. 145 | CF₃ | H | —SCH(CH₃)—CO—OCH(CH₃)—CO—OCH₃ | |
| Ia. 146 | Cl | H | —SCH(CH₃)—CO—OCH(CH₃)—CO—OCH₃ | |
| Ia. 147 | CF₃ | F | —SCH(CH₃)—CO—OCH(CH₃)—CO—OCH₃ | |
| Ia. 148 | Cl | F | —SCH(CH₃)—CO—OCH(CH₃)—CO—OCH₃ | |
| Ia. 149 | CF₃ | Cl | —SCH(CH₃)—CO—OCH(CH₃)—CO—OCH₃ | |
| Ia. 150 | Cl | Cl | —SCH(CH₃)—CO—OCH(CH₃)—CO—OCH₃ | |
| Ia. 151 | CF₃ | H | —SCH(CH₃)—CO—OCH(CH₃)—CO—OC₂H₅ | |
| Ia. 152 | Cl | H | —SCH(CH₃)—CO—OCH(CH₃)—CO—OC₂H₅ | |
| Ia. 153 | CF₃ | F | —SCH(CH₃)—CO—OCH(CH₃)—CO—OC₂H₅ | |
| Ia. 154 | Cl | F | —SCH(CH₃)—CO—OCH(CH₃)—CO—OC₂H₅ | |
| Ia. 155 | CF₃ | Cl | —SCH(CH₃)—CO—OCH(CH₃)—CO—OC₂H₅ | |
| Ia. 156 | Cl | Cl | —SCH(CH₃)—CO—OCH(CH₃)—CO—OC₂H₅ | |
| Ia. 157 | CF₃ | H | —SCH₂—CO—OCH₂—CO—N(CH₃)₂ | |
| Ia. 158 | Cl | H | —SCH₂—CO—OCH₂—CO—N(CH₃)₂ | |
| Ia. 159 | CF₃ | F | —SCH₂—CO—OCH₂—CO—N(CH₃)₂ | |
| Ia. 160 | Cl | F | —SCH₂—CO—OCH₂—CO—N(CH₃)₂ | |
| Ia. 161 | CF₃ | Cl | —SCH₂—CO—OCH₂—CO—N(CH₃)₂ | |
| Ia. 162 | Cl | Cl | —SCH₂—CO—OCH₂—CO—N(CH₃)₂ | |
| Ia. 163 | CF₃ | H | —SCH₂—CO—OCH(CH₃)—CO—N(CH₃)₂ | |
| Ia. 164 | Cl | H | —SCH₂—CO—OCH(CH₃)—CO—N(CH₃)₂ | |
| Ia. 165 | CF₃ | F | —SCH₂—CO—OCH(CH₃)—CO—N(CH₃)₂ | |
| Ia. 166 | Cl | F | —SCH₂—CO—OCH(CH₃)—CO—N(CH₃)₂ | |
| Ia. 167 | CF₃ | Cl | —SCH₂—CO—OCH(CH₃)—CO—N(CH₃)₂ | |
| Ia. 168 | Cl | Cl | —SCH₂—CO—OCH(CH₃)—CO—N(CH₃)₂ | |
| Ia. 169 | CF₃ | H | —SCH(CH₃)—CO—OCH₂—CO—N(CH₃)₂ | |
| Ia. 170 | Cl | H | —SCH(CH₃)—CO—OCH₂—CO—N(CH₃)₂ | |
| Ia. 171 | CF₃ | F | —SCH(CH₃)—CO—OCH₂—CO—N(CH₃)₂ | |
| Ia. 172 | Cl | F | —SCH(CH₃)—CO—OCH₂—CO—N(CH₃)₂ | |
| Ia. 173 | CF₃ | Cl | —SCH(CH₃)—CO—OCH₂—CO—N(CH₃)₂ | |
| Ia. 174 | Cl | Cl | —SCH(CH₃)—CO—OCH₂—CO—N(CH₃)₂ | |
| Ia. 175 | CF₃ | H | —SCH(CH₃)—CO—OCH(CH₃)—CO—N(CH₃)₂ | |
| Ia. 176 | Cl | H | —SCH(CH₃)—CO—OCH(CH₃)—CO—N(CH₃)₂ | |
| Ia. 177 | CF₃ | F | —SCH(CH₃)—CO—OCH(CH₃)—CO—N(CH₃)₂ | |
| Ia. 178 | Cl | F | —SCH(CH₃)—CO—OCH(CH₃)—CO—N(CH₃)₂ | |
| Ia. 179 | CF₃ | Cl | —SCH(CH₃)—CO—OCH(CH₃)—CO—N(CH₃)₂ | |
| Ia. 180 | Cl | Cl | —SCH(CH₃)—CO—OCH(CH₃)—CO—N(CH₃)₂ | |
| Ia. 181 | CF₃ | H | —CO—OCH(CH₃)—CO—OH | |
| Ia. 182 | Cl | H | —CO—OCH(CH₃)—CO—OH | |
| Ia. 183 | CF₃ | F | —CO—OCH(CH₃)—CO—OH | oil |
| Ia. 184 | Cl | F | —CO—OCH(CH₃)—CO—OH | |
| Ia. 185 | CF₃ | Cl | —CO—OCH(CH₃)—CO—OH | |
| Ia. 186 | Cl | Cl | —CO—OCH(CH₃)—CO—OH | |
| Ia. 187 | CF₃ | H | —CO—OCH(CH₃)—CO—OCH(CH₃)₂ | |
| Ia. 188 | Cl | H | —CO—OCH(CH₃)—CO—OCH(CH₃)₂ | |
| Ia. 189 | CF₃ | F | —CO—OCH(CH₃)—CO—OCH(CH₃)₂ | oil |
| Ia. 190 | Cl | F | —CO—OCH(CH₃)—CO—OCH(CH₃)₂ | |
| Ia. 191 | CF₃ | Cl | —CO—OCH(CH₃)—CO—OCH(CH₃)₂ | |
| Ia. 192 | Cl | Cl | —CO—OCH(CH₃)—CO—OCH(CH₃)₂ | |
| Ia. 193 | CF₃ | H | —CO—OCH(CH₃)—CO—OCH₂—CH=CH₂ | |
| Ia. 194 | Cl | H | —CO—OCH(CH₃)—CO—OCH₂—CH=CH₂ | |
| Ia. 195 | CF₃ | F | —CO—OCH(CH₃)—CO—OCH₂—CH=CH₂ | oil |
| Ia. 196 | Cl | F | —CO—OCH(CH₃)—CO—OCH₂—CH=CH₂ | |
| Ia. 197 | CF₃ | Cl | —CO—OCH(CH₃)—CO—OCH₂—CH=CH₂ | |

TABLE 1-continued

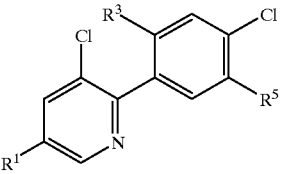

(Ia)

| No. | R¹ | R³ | R⁵ | M.p. [° C.] |
|---|---|---|---|---|
| Ia. 198 | Cl | Cl | —CO—OCH(CH₃)—CO—OCH₂—CH=CH₂ | |
| Ia. 199 | CF₃ | H | —CO—OCH₂—CO—OCH₂—CH₂—CH₂—C₂H₅ | |
| Ia. 200 | Cl | H | —CO—OCH₂—CO—OCH₂—CH₂—CH₂—C₂H₅ | |
| Ia. 201 | CF₃ | F | —CO—OCH₂—CO—OCH₂—CH₂—CH₂—C₂H₅ | oil |
| Ia. 202 | Cl | F | —CO—OCH₂—CO—OCH₂—CH₂—CH₂—C₂H₅ | |
| Ia. 203 | CF₃ | Cl | —CO—OCH₂—CO—OCH₂—CH₂—CH₂—C₂H₅ | |
| Ia. 204 | Cl | Cl | —CO—OCH₂—CO—OCH₂—CH₂—CH₂—C₂H₅ | |
| Ia. 205 | CF₃ | H | —CO—OCH(CH₃)—CO—OCH₂—CH(CH₃)₂ | |
| Ia. 206 | Cl | H | —CO—OCH(CH₃)—CO—OCH₂—CH(CH₃)₂ | |
| Ia. 207 | CF₃ | F | —CO—OCH(CH₃)—CO—OCH₂—CH(CH₃)₂ | oil |
| Ia. 208 | Cl | F | —CO—OCH(CH₃)—CO—OCH₂—CH(CH₃)₂ | |
| Ia. 209 | CF₃ | Cl | —CO—OCH(CH₃)—CO—OCH₂—CH(CH₃)₂ | |
| Ia. 210 | Cl | Cl | —CO—OCH(CH₃)—CO—OCH₂—CH(CH₃)₂ | |
| Ia. 211 | CF₃ | H | —CO—OCH(CH₃)—CO—NH₂ | |
| Ia. 212 | Cl | H | —CO—OCH(CH₃)—CO—NH₂ | |
| Ia. 213 | CF₃ | F | —CO—OCH(CH₃)—CO—NH₂ | oil |
| Ia. 214 | Cl | F | —CO—OCH(CH₃)—CO—NH₂ | |
| Ia. 215 | CF₃ | Cl | —CO—OCH(CH₃)—CO—NH₂ | |
| Ia. 216 | Cl | Cl | —CO—OCH(CH₃)—CO—NH₂ | |
| Ia. 217 | CF₃ | H | —OCH₂—CO—OCH₂—CO—OCH(CH₃)₂ | |
| Ia. 218 | Cl | H | —OCH₂—CO—OCH₂—CO—OCH(CH₃)₂ | |
| Ia. 219 | CF₃ | F | —OCH₂—CO—OCH₂—CO—OCH(CH₃)₂ | 58–59 |
| Ia. 220 | Cl | F | —OCH₂—CO—OCH₂—CO—OCH(CH₃)₂ | |
| Ia. 221 | CF₃ | Cl | —OCH₂—CO—OCH₂—CO—OCH(CH₃)₂ | |
| Ia. 222 | Cl | Cl | —OCH₂—CO—OCH₂—CO—OCH(CH₃)₂ | |
| Ia. 223 | CF₃ | H | —OCH₂—CO—OCH(CH₃)—CO—OCH(CH₃)₂ | |
| Ia. 224 | Cl | H | —OCH₂—CO—OCH(CH₃)—CO—OCH(CH₃)₂ | |
| Ia. 225 | CF₃ | F | —OCH₂—CO—OCH(CH₃)—CO—OCH(CH₃)₂ | 66–67 |
| Ia. 226 | Cl | F | —OCH₂—CO—OCH(CH₃)—CO—OCH(CH₃)₂ | |
| Ia. 227 | CF₃ | Cl | —OCH₂—CO—OCH(CH₃)—CO—OCH(CH₃)₂ | |
| Ia. 228 | Cl | Cl | —OCH₂—CO—OCH(CH₃)—CO—OCH(CH₃)₂ | |
| Ia. 229 | CF₃ | H | —OCH₂—CO—OCH(CH₃)—CO—OCH₂—CH=CH₂ | |
| Ia. 230 | Cl | H | —OCH₂—CO—OCH(CH₃)—CO—OCH₂—CH=CH₂ | |
| Ia. 231 | CF₃ | F | —OCH₂—CO—OCH(CH₃)—CO—OCH₂—CH=CH₂ | 92–93 |
| Ia. 232 | Cl | F | —OCH₂—CO—OCH(CH₃)—CO—OCH₂—CH=CH₂ | |
| Ia. 233 | CF₃ | Cl | —OCH₂—CO—OCH(CH₃)—CO—OCH₂—CH=CH₂ | |
| Ia. 234 | Cl | Cl | —OCH₂—CO—OCH(CH₃)—CO—OCH₂—CH=CH₂ | |
| Ia. 235 | CF₃ | H | —OCH(CH₃)—CO—OCH(CH₃)—CO—OCH(CH₃)₂ | |
| Ia. 236 | Cl | H | —OCH(CH₃)—CO—OCH(CH₃)—CO—OCH(CH₃)₂ | |
| Ia. 237 | CF₃ | F | —OCH(CH₃)—CO—OCH(CH₃)—CO—OCH(CH₃)₂ | oil |
| Ia. 238 | Cl | F | —OCH(CH₃)—CO—OCH(CH₃)—CO—OCH(CH₃)₂ | |
| Ia. 239 | CF₃ | Cl | —OCH(CH₃)—CO—OCH(CH₃)—CO—OCH(CH₃)₂ | |
| Ia. 240 | Cl | Cl | —OCH(CH₃)—CO—OCH(CH₃)—CO—OCH(CH₃)₂ | |
| Ia. 241 | CF₃ | H | —OCH(CH₃)—CO—OCH(CH₃)—CO—OCH₂—CH=CH₂ | |
| Ia. 242 | Cl | H | —OCH(CH₃)—CO—OCH(CH₃)—CO—OCH₂—CH=CH₂ | |
| Ia. 243 | CF₃ | F | —OCH(CH₃)—CO—OCH(CH₃)—CO—OCH₂—CH=CH₂ | oil |
| Ia. 244 | Cl | F | —OCH(CH₃)—CO—OCH(CH₃)—CO—OCH₂—CH=CH₂ | |
| Ia. 245 | CF₃ | Cl | —OCH(CH₃)—CO—OCH(CH₃)—CO—OCH₂—CH=CH₂ | |
| Ia. 246 | Cl | Cl | —OCH(CH₃)—CO—OCH(CH₃)—CO—OCH₂—CH=CH₂ | |
| Ia. 247 | CF₃ | H | —OCH₂—CO—OC(CH₃)₂—CO—OH | |
| Ia. 248 | Cl | H | —OCH₂—CO—OC(CH₃)₂—CO—OH | |
| Ia. 249 | CF₃ | F | —OCH₂—CO—OC(CH₃)₂—CO—OH | oil |
| Ia. 250 | Cl | F | —OCH₂—CO—OC(CH₃)₂—CO—OH | |
| Ia. 251 | CF₃ | Cl | —OCH₂—CO—OC(CH₃)₂—CO—OH | |
| Ia. 252 | Cl | Cl | —OCH₂—CO—OC(CH₃)₂—CO—OH | |
| Ia. 253 | CF₃ | H | —OCH₂—CO—OC(CH₃)₂—CO—OCH₃ | |
| Ia. 254 | Cl | H | —OCH₂—CO—OC(CH₃)₂—CO—OCH₃ | |
| Ia. 255 | CF₃ | F | —OCH₂—CO—OC(CH₃)₂—CO—OCH₃ | oil |
| Ia. 256 | Cl | F | —OCH₂—CO—OC(CH₃)₂—CO—OCH₃ | |
| Ia. 257 | CF₃ | Cl | —OCH₂—CO—OC(CH₃)₂—CO—OCH₃ | |
| Ia. 258 | Cl | Cl | —OCH₂—CO—OC(CH₃)₂—CO—OCH₃ | |
| Ia. 259 | CF₃ | H | —OCH₂—CO—OC(CH₃)₂—CO—OC₂H₅ | |
| Ia. 260 | Cl | H | —OCH₂—CO—OC(CH₃)₂—CO—OC₂H₅ | |
| Ia. 261 | CF₃ | F | —OCH₂—CO—OC(CH₃)₂—CO—OC₂H₅ | oil |
| Ia. 262 | Cl | F | —OCH₂—CO—OC(CH₃)₂—CO—OC₂H₅ | |
| Ia. 263 | CF₃ | Cl | —OCH₂—CO—OC(CH₃)₂—CO—OC₂H₅ | |

TABLE 1-continued (Ia)

[Structure: 2-phenylpyridine with R¹, Cl on pyridine; R³, Cl, R⁵ on phenyl]

| No. | R¹ | R³ | R⁵ | M.p. [° C.] |
|---|---|---|---|---|
| Ia. 264 | Cl | Cl | —OCH$_2$—CO—OC(CH$_3$)$_2$—CO—OC$_2$H$_5$ | |
| Ia. 265 | CF$_3$ | H | —OCH(CH$_3$)—CO—OC(CH$_3$)$_2$—CO—OH | |
| Ia. 266 | Cl | H | —OCH(CH$_3$)—CO—OC(CH$_3$)$_2$—CO—OH | |
| Ia. 267 | CF$_3$ | F | —OCH(CH$_3$)—CO—OC(CH$_3$)$_2$—CO—OH | 160–162 |
| Ia. 269 [sic] | Cl | F | —OCH(CH$_3$)—CO—OC(CH$_3$)$_2$—CO—OH | |
| Ia. 269 | CF$_3$ | Cl | —OCH(CH$_3$)—CO—OC(CH$_3$)$_2$—CO—OH | |
| Ia. 270 | Cl | Cl | —OCH(CH$_3$)—CO—OC(CH$_3$)$_2$—CO—OH | |
| Ia. 271 | CF$_3$ | H | —OCH(CH$_3$)—CO—OC(CH$_3$)$_2$—CO—OCH$_3$ | |
| Ia. 272 | Cl | H | —OCH(CH$_3$)—CO—OC(CH$_3$)$_2$—CO—OCH$_3$ | |
| Ia. 273 | CF$_3$ | F | —OCH(CH$_3$)—CO—OC(CH$_3$)$_2$—CO—OCH$_3$ | oil |
| Ia. 274 | Cl | F | —OCH(CH$_3$)—CO—OC(CH$_3$)$_2$—CO—OCH$_3$ | |
| Ia. 275 | CF$_3$ | Cl | —OCH(CH$_3$)—CO—OC(CH$_3$)$_2$—CO—OCH$_3$ | |
| Ia. 276 | Cl | Cl | —OCH(CH$_3$)—CO—OC(CH$_3$)$_2$—CO—OCH$_3$ | |
| Ia. 277 | CF$_3$ | H | —OCH(CH$_3$)—CO—OC(CH$_3$)$_2$—CO—OC$_2$H$_5$ | |
| Ia. 278 | Cl | H | —OCH(CH$_3$)—CO—OC(CH$_3$)$_2$—CO—OC$_2$H$_5$ | |
| Ia. 279 | CF$_3$ | F | —OCH(CH$_3$)—CO—OC(CH$_3$)$_2$—CO—OC$_2$H$_5$ | oil |
| Ia. 280 | Cl | F | —OCH(CH$_3$)—CO—OC(CH$_3$)$_2$—CO—OC$_2$H$_5$ | |
| Ia. 281 | CF$_3$ | Cl | —OCH(CH$_3$)—CO—OC(CH$_3$)$_2$—CO—OC$_2$H$_5$ | |
| Ia. 282 | Cl | Cl | —OCH(CH$_3$)—CO—OC(CH$_3$)$_2$—CO—OC$_2$H$_5$ | |

Especially preferred are, furthermore, the substituted 2-phenylpyridines Ib, in particular the compounds Ib.01 to Ib.282, which only differ from the corresponding compounds Ia.01 to Ia.282 by the fact that $R^4$ is cyano:

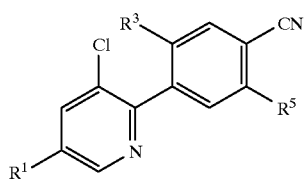

($R^2$ = Cl, $R^4$ = CN)

The substituted 2-phenylpyridines of the formula I can be obtained in various ways, for example by one of the following processes:

Process A

Reaction of acid chlorides IIa or IIc with hydroxycarboxylic acids/hydroxycarboxylic acid derivatives IIIa or IIIb, or of acid chlorides IIb with alcohols IIIc or amines IIId, in the presence of a base (cf., for example, K. Furuta et al., Org. Synth. 72, 86 (1993) and H. Henecka in Houben-Weyl, Methoden der Organischen Chemie [Methods in Organic Chemistry], Vol. VIII, 4th Edition Stuttgart 1952, pages 463 et seq.):

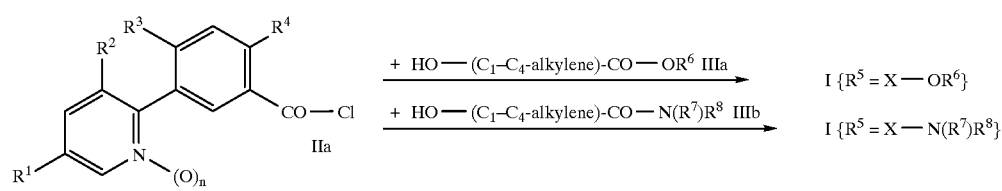

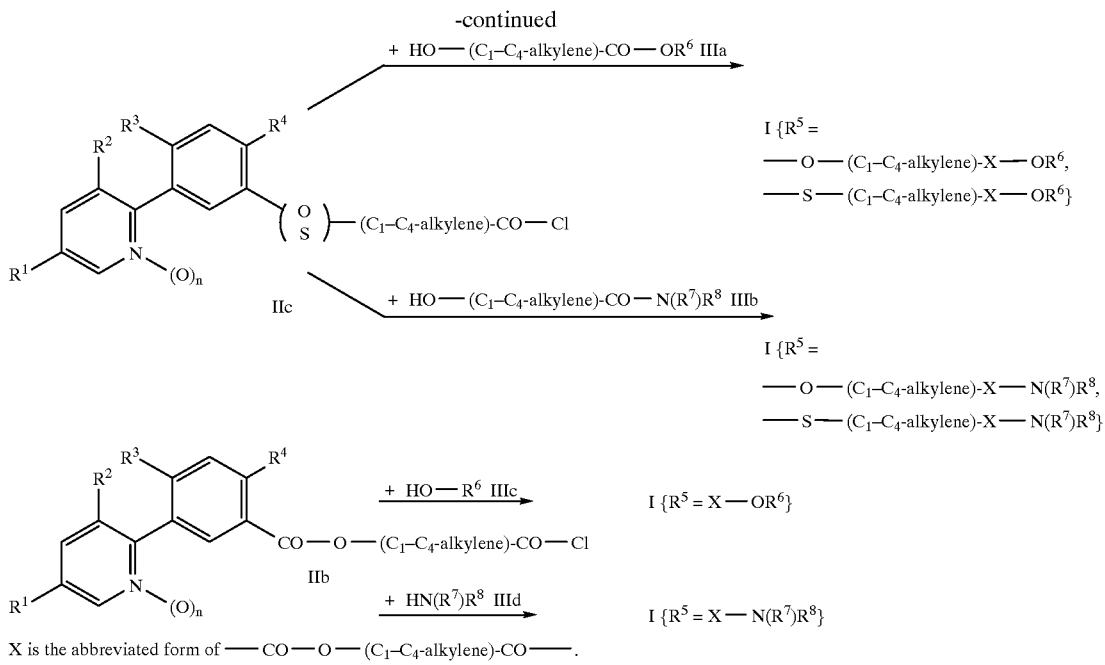

X is the abbreviated form of —CO—O—(C$_1$–C$_4$-alkylene)-CO—.

The process is usually carried out in an inert solvent or diluent, in particular in a halogenated hydrocarbon such as dichloromethane, chloroform, 1,2-dichloroethane and carbon tetrachloride.

Examples of suitable bases are alkali metal (hydrogen) carbonates such as sodium hydrogen carbonate and sodium carbonate, furthermore nitrogen bases such as pyridine, 4-dimethylaminopyridine and triethylamine.

The reaction temperature is normally from 0 to 100° C.

The reactants are usually employed in approximately stoichiometric ratios, but an excess of one of the reactants may be advantageous, for example with a view to as complete as possible a reaction of the other reactant.

The acid chlorides of the formula IIa and IIc are disclosed in the earlier German Application DE-A 19 500 758. The acid chlorides IIb are novel and expediently obtainable by reacting IIa with hydroxycarboxylic acids HO-(C$_1$–C$_4$-alkylene)-COOH (IV) or their salts followed by chlorination of the resulting process products (V):

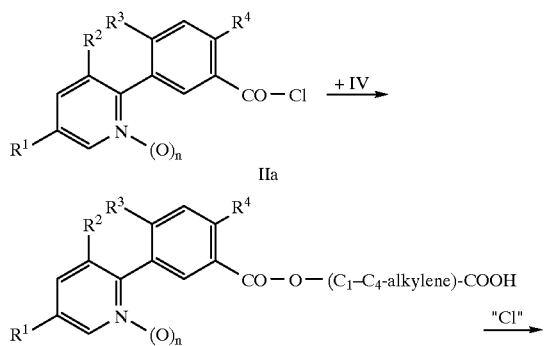

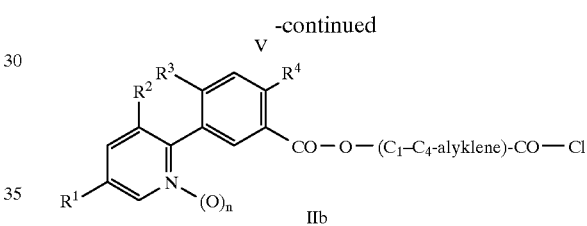

Useful salts of IV are mainly the alkali metal salts, in particular the sodium and potassium salts.

The chlorination can be carried out either without a solvent in an excess of the halogenating agent or in an inert solvent or diluent, in particular in an aprotic solvent, eg. diethyl ether, benzene or carbon disulfide.

Suitable chlorinating agents are, for example, thionyl chloride, oxalyl chloride, phosphorus trichloride, phosphorus pentachloride, phosphorus oxychloride, phosgene, diphosgene or triphosgene.

Other information for carrying out such chlorination reactions can be found in the literature which follows and to which reference is made by way of example:

A. J. Meyers and M. E. Flanagan, Org. Synth. 71, 107 (1992);

H. J. Scheifele Jr. and D. F. DeTar, Org. Synth. Coll. Vol. IV, page 34 (1963);

G. H. Coleman et al., Org. Synth. Coll. Vol. III, page 712 (1955);

H. Henecka in Houben-Weyl, Methoden der Organischen Chemie [Methods in Organic Chemistry], Vol. VIII, 4th Edition Stuttgart 1952, pages 463 et seq.

The carboxylic acids which correspond to the acid chlorides III which are not disclosed, for example, in DE-A 43 23 916, equivalent to U.S. Pat. No. 5,783,522 can be obtained in the manner described in this publication.

Process B

Oxidation of substituted 2-phenylpyridines of the formula I where n is zero and the substituent R$^5$ does not contain a sulfur bridge in a manner known per se {cf., for example, A. Albini & S. Pietra, Heterocyclic N-Oxides, CRC-Press Inc., Boca Raton, U.S.A 1991; H. S. Mosher et al., Org. Synth. Coll. Vol. IV 1963, page 828; E. C. Taylor et al., Org. Synth. Coll. Vol. IV 1963, page 704; T. W. Bell et al., Org. Synth. 69, page 226 (1990)}:

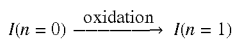

Amongst the oxidants conventionally used for oxidizing the pryidine ring, reference may be made for example to peracetic acid, trifluoroperacetic acid, perbenzoic acid, m-chloroperbenzoic acid, monopermaleic acid, magnesium monoperphthalate, sodium perborate, Oxone® (contains peroxydisulfate), pertungstic acid and hydrogen peroxide.

Examples of suitable solvents are water, sulfuric acid, carboxylic acids such as acetic acid and trifluoroacetic acid, and halogenated hydrocarbons such as dichloromethane and chloroform.

The oxidation is normally successfully carried out at from 0° C. to the boiling point of the reaction mixture.

The oxidant is normally employed in at least equimolar amounts based on the starting compound. In general, an excess of oxidant has proved to be particularly advantageous.

Process C

Reaction of 3-pyridylphenols of the formula VI with electrophiles of the formula VII or VIII in the presence of a base:

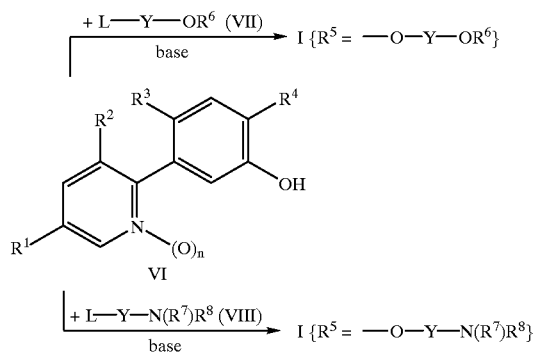

Y is the chain -($C_1$–$C_4$-alkylene)-CO—O-($C_1$–$C_4$-alkylene)-CO—.

L is chlorine, bromine, iodine, methylsulfonyloxy, trifluoromethylsulfonyloxy, phenylsulfonyloxy or p-tolylsulfonyloxy.

As a rule, the process is carried out in an inert solvent or diluent which is preferably aprotic, eg. in N,N-dimethylformamide, dimethyl sulfoxide, acetone, N-methylpyrrolidone, acetonitrile, or in an ether such as diethyl ether, tetrahydrofuran and 1,4-dioxane.

Examples of useful bases are alkali metal carbonates and alkali metal hydrogen carbonates such as sodium hydrogen carbonate, potassium hydrogen carbonate, sodium carbonate and potassium carbonate, alkali metal alcoholates such as sodium methanolate and potassium tert-butanolate, alkali metal hydroxides such as sodium hydroxide, and alkali metal hydrides such as sodium hydride.

Other information for carrying out such alkylation reactions can be found, for example, in the literature which follows:

* re: alkylation of phenols with α-carbonylsulfonates:
  U. Burkard and F. Effenberger, Chem. Ber. 119, 1594 (1986);
  J. Bierdermann et al., J. Med. Chem. 29, 1183 (1986);
  R. B. Rogers et al., U.S. Pat. No. 4,725,683.
** re: alkylation of phenols with α-haloesters:
  R. Aneja et al., Tetrahedron 2, 203 (1958);
  EP-A 380 043;
  C. R. Edwards et al., J. Heterocycl. Chem. 24, 495 (1987);
  C. P. Phadke et al., Synthesis 5, 413 (1986);
  K. G. Watson, U.S. Pat. No. 4,837,355;
  V. Elango et al., U.S. Pat. No. 4,908,476;
  G. Schlegel et al., U.S. Pat. No. 4,978,774;
  U. Burkard and F. Effenberger, Chem. Ber. 119, 1594 (1986);
  H. Sugihara et al., Chem. And Pharm. Bull. 35, 1919 (1987);
  S. Fujinawa et al., U.S. Pat. No. 4,625,053.

Those electrophiles VII and VIII which are not already known can be obtained in a known manner {cf., for example, in this context EP-A 537 838; E. K. Euranto, Suom. Kemistilehti B 43(9), 324–327 (1970); DE-A 43 20 396; JP 04/001 190; DE-A 25 01 448; U.S. Pat. No. 4,033,938; M. Franck-Neumann et al., Synlett 10, 637–640 (1990); J. H. Clark et al., J. Chem. Soc., Dalton Trans. 20, 2129–2134 (1975) and FR 2 459 221}.

Process D

Reaction of 3-pyridylthiophenols of the formula IX with electrophiles VII or VIII in the presence of a base:

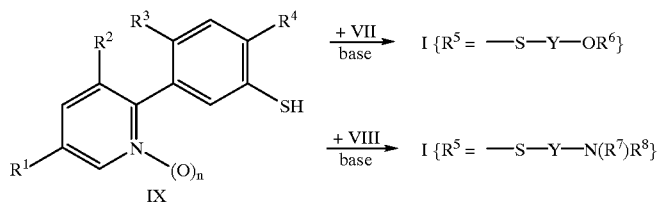

Regarding the definition of Y and L and suitable solvents/diluents and bases, the information given for process C) also applies here.

Other information for carrying out such alkylation reactions can be found, for example, in the literature which follows:

* re: alkylation of thiophenols with α-carbonylsulfonates:

U. Burkard and F. Effenberger, Chem. Ber. 119, 1594 (1986);

** re: alkylation of thiophenols with α-haloesters:

M. B. Floyd, U.S. Pat. No. 4,983,753;

E. Campaigne and A. R. McLaughlin, J. Heterocycl. Chem. 20, 623 (1983);

J. Durman et al., J. Chem. Soc. Perkin Trans., 1939 (1986);

M. Kawada et al., Chem. Pharm. Bull. 34, 1939 (1986);

H. Sugihara et al., Chem. and Pharm. Bull. 35, 1919 (1987).

Unless otherwise specified, all processes described above are expediently carried out under atmospheric pressure or under the inherent pressure of the reaction mixture in question.

The substituted 2-phenylpyridines I can normally be prepared by one of the synthesis methods mentioned above. For economical or technological reasons, however, it may be more expedient to prepare some compounds I from 2-phenylpyridines which are similar but which differ with regard to the meaning of one radical.

As a rule, the reaction mixtures are worked up by methods known per se, for example by diluting the reaction solution with water and subsequently isolating the product by means of filtration, crystallization or solvent extraction, or by removing the solvent, partitioning the residue in a mixture of water and a suitable organic solvent, and working up the organic phase so as to obtain the product.

The substituted 2-phenylpyridines of the formula I can contain one or more chiral centers, in which case they are usually obtained as enantiomer or diastereomer mixtures. If desired, the mixtures can be separated into the essentially pure isomers by the methods customary for this purpose, such as crystallization or chromatography, even on an optically active adsorbate. Pure optically active isomers may, for example, also be prepared from suitable optically active starting materials.

Those substituted 2-phenylpyridines I where $R^6$=hydrogen can be converted into their salts, preferably their alkali metal salts, in a manner known per se.

Salts of I whose metal ion is not an alkali metal ion can be prepared in a conventional manner by double decomposition of the corresponding alkali metal salt, and ammonium, phosphonium, sulfonium and sulfoxonium salts by means of ammonia, or phosphonium, sulfonium or sulfoxonium hydroxides.

The compounds I and their agriculturally useful salts, in the form of isomer mixtures and also in the form of the pure isomers, are suitable as herbicides. The herbicidal compositions comprising I are capable of effecting very good vegetation control in non-crop areas, especially at high rates of application. In crops such as wheat, rice, maize, soya and cotton, they act against broad-leaved weeds and grass weeds without inflicting substantial damage to the crop plants. This effect is observed especially at low rates of application.

Depending on the application method in question, the compounds I, or herbicidal compositions comprising them, can also be employed in a further number of crop plants for eliminating undesirable plants. Suitable crops are, for example, the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,*(*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec, *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (s. *vulgare*), *Theobroma cacao, Trifolium pratense, Triticum aestivum, Triticum durum, Vicia faba, Vitis vinifera* and *Zea mays.*

In addition, the compounds I can also be used in crops which tolerate the action of herbicides due to breeding, including genetic engineering methods.

Furthermore, the substituted 2-phenylpyridines I are also suitable for the desiccation and/or defoliation of plants.

As desiccants, they are particularly suitable for the desiccation of the aerial parts of crop plants such as potatoes, oil seed rape, sunflowers and soya beans. This allows completely mechanical harvesting of these important crop plants.

It is also of economic interest to facilitate harvesting, which is made possible by concentrating, over a period of time, dehiscence, or reduction of the adherence to the tree, in citrus fruit, olives or other species and varieties of pomacious fruit, stone fruit and nuts. The same mechanism, ie. promotion of the formation of abscission tissue between fruit or leaf and shoot of the plants is also important for readily controllable defoliation of useful plants, in particular cotton.

Moreover, shortening the period within which the individual cotton plants mature results in an improved fiber quality after harvesting.

The compounds I, or the compositions comprising them, can be used for example in the form of ready-to-spray aqueous solutions, powders, suspensions, also highly concentrated aqueous, oily or other suspensions or dispersions, emulsions, oil dispersions, pastes, dusts, materials for spreading or granules, by means of spraying, atomizing, dusting, spreading or pouring. The use forms depend on the intended aims; in any case, they should guarantee the finest possible distribution of the active ingredients according to the invention.

Suitable inert auxiliaries for the preparation of ready-to-spray solutions, emulsions, pastes or oil dispersions are mainly: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the active ingredient, as such or dissolved in an oil or solvent, can be homogenized in water by means of wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders or others.

The concentrations of the active ingredients I in the ready-to-use preparations can be varied within wide limits. The formulations generally comprise from about 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples which follow illustrate the preparation of such products:

I. 20 parts by weight of the compound No. Ia.09 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. Ia.15 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. Ia.39 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. Ia.51 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. Ia.57 are mixed with 97 parts by weight of finely divided kaolin. This gives a dust which comprises 3% by weight of the active ingredient.

VI. 20 parts by weight of the active ingredient No. Ia.81 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active ingredient No. Ia.195 is dissolved in a mixture composed of 70 parts by weight of cyclohexanone, 20 parts by weight of ethoxylated isooctylphenol and 10 parts by weight of ethoxylated castor oil. This gives a stable emulsion concentrate which can be diluted with water to give the desired concentration of active ingredient.

VIII. 1 part by weight of the active ingredient No. Ia.261 is dissolved in a mixture composed of 80 parts by weight of cyclohexanone and 20 parts by weight of Wettol® EM 31 (=nonionic emulsifier based on ethoxylated castor oil; BASF AG). This gives a stable emulsion concentrate.

The active ingredients I, or the herbicidal compositions, can be applied pre- or post-emergence. If the active ingredients are less well tolerated by certain crop plants, application techniques may be used in which the herbicidal compositions are sprayed, with the aid of the spraying equipment, in such a way that the active ingredients come into as little contact as possible with the leaves of the sensitive crop plants, while reaching the leaves of undesirable plants which grow underneath, or the bare soil (post-directed, lay-by).

Depending on the intended aim, the season, the target plants and the growth stage, the application rates of active ingredient I are from 0.001 to 3.0, preferably 0.01 to 1, kg/ha of active ingredient (a.i.).

To widen the spectrum of action and to achieve synergistic effects, the substituted 2-phenylpyridines I may be mixed with a large number of representatives of groups of other herbicidal or growth-regulating active ingredients and applied concomitantly. Suitable components for mixtures are, for example, 1,2,4-thia-diazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6- tetrahydrophthalimides, oxadiazoles, oxiranes, phenols, aryloxy- and hetaryloxyphenoxypropionates, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, together with further crop protection agents in the form of a mixture, for example with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

PREPARATION EXAMPLES

Example 1
Compound No. Ia.09 in Table 1
3.0 g of 3-chloro-2-(5-carboxy-4-chloro-2-fluorophenyl)-5-trifluoromethylpyridine were refluxed for 2.5 hours in 20 ml of thionyl chloride. The excess thionyl chloride was then distilled off under reduced pressure, whereupon the residue was dissolved in 25 ml of anhydrous methylene chloride. After 0.8 g of pyridine and 5.0 g of ethyl glycolate had been added, the reaction mixture was refluxed for a further 7.5 hours and then stirred at 23° C. for approximately 15 hours.

For working-up, the reaction batch was first concentrated under reduced pressure. After the residue had been taken up in 50 ml of methylene chloride, the mixture was extracted using 50 ml of 0.1-molar hydrochloric acid and 50 ml of water in succession. The organic phase was subsequently dried over sodium sulfate and then concentrated. The residue was purified by silica gel chromatography (eluent:cyclohexane/ethyl acetate=10:1). Yield: 2.3 g of colorless crystals; melting point: 68° C.
$^1$H NMR (200 MHz, in CDCl$_3$): δ[ppm]=1.30 (t,3H), 4.27 (q,2H), 4.85 (s,2H), 7.37 (d,1H), 8.08 (s,1H), 8.20 (d,1H), 8.90 (s,1H).

Example 2
Compound No. Ia.15 in Table 1
By a method similar to the method in Example 1, 1.9 g of a colorless oil were obtained using 3.0 g of 3-chloro-2-(5-carboxy-4-chloro-2-fluorophenyl)-5-trifluoromethyl-pyridine, 1.35 g of pyridine and 1.77 g of methyl(s)-lactate.
$^1$H NMR (200 MHz, in CDCl$_3$): δ[ppm]=1.63 (d,3H), 3.78 (s,3H), 5.35 (q,1H), 7.37 (d,1H), 8.08 (s,1H), 8.17 (d,1H), 8.88 (s,1H).
Use Examples (herbicidal activity)

The herbicidal action of the substituted 2-phenylpyridines I was demonstrated by the following greenhouse experiments:

The culture containers used were plastic flowerpots containing loamy sand with approximately 3.0% of humus as the substrate. The seeds of the test plants were sown separately for each species.

In the case of pre-emergence treatment, the active ingredients which had been suspended or emulsified in water were applied directly after sowing by means of finely distributing nozzles. The containers were irrigated gently to promote germination and growth and subsequently covered with translucent plastic hoods until the plants had rooted. This cover results in uniform germination of the test plants, unless germination was adversely affected by the active ingredients.

For post-emergence treatment, the test plants were first grown to a plant height of 3 to 15 cm, depending on the plant habit, and only then treated with the active ingredients which had been suspended or emulsified in water. The test plants were either sown directly and grown in the same containers, or grown separately as seedlings and transplanted to the test containers a few days prior to treatment. The rate of application for the post-emergence treatment was 0.98 or 0.49 g/ha of a.i (active ingredient).

The plants were kept at 10–25° C. or 20–35° C., depending on the species. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific Name | Common Name |
| --- | --- |
| Galium aparine | catchweed bedstraw |
| Ipomoea subspecies | morning glory |
| Polygonum persicaria | lady's thumb |
| Sinapis alba | white mustard |

At a rate of application of 0.98 or 0.49 g/ha of a.i., the compound No. Ia.15 showed a good to very good activity against the abovementioned plants when used post-emergence.

In contrast, the compound

Comparison Compound A

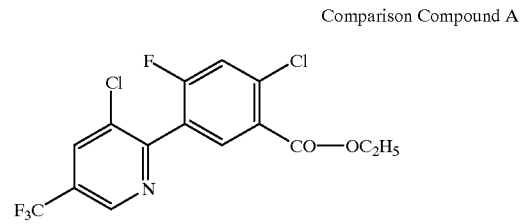

disclosed in WO 95/02580 (No. 1.599 in this publication) and also tested for comparison reasons was less effective.

Use Examples (desiccant/defoliant activity)

The test plants used were young cotton plants with 4 leaves (without cotyledons) which were grown under greenhouse conditions (relative atmospheric humidity 50 to 70%; day/night temperature 27/20° C.).

The young cotton plants were subjected to foliar treatment to drip point with aqueous preparations of the active ingredients (with an addition of 0.15% by weight of the fatty alcohol alkoxylate Plurafac® LF 700$^1$), based on the spray mixture). The amount of water applied was 1000 l/ha (converted). After 13 days, the number of leaves shed and the degree of defoliation in % were determined.

1) a low-foam, nonionic surfactant from BASF AG

No leaves were shed in the untreated control plants.

We claim:

1. A substituted 2-phenylpyridine of the general formula I

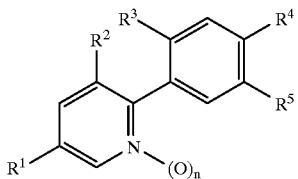

where the variables have the following meanings:

n is 0 or 1;

$R^1$ is halogen or $C_1$–$C_4$-haloalkyl;

$R^2$ and $R^3$ are in each case hydrogen or halogen;

$R^4$ is cyano or halogen;

$R^5$ is —CO—O-($C_1$–$C_4$-alkylene)-CO—$OR^6$, —CO—O-($C_1$–$C_4$-alkylene)-CO—N($R^7$)$R^8$, —O-($C_1$–$C_4$-alkylene)-CO—O-($C_1$–$C_4$-alkylene)-CO—$OR^6$, —O-($C_1$–$C_4$-alkylene)-CO—O-($C_1$–$C_4$-alkylene)-CO—N($R^7$)$R^8$, —S-($C_1$–$C_4$-alkylene)-CO—O-($C_1$–$C_4$-alkylene)-CO—$OR^6$ or —S-($C_1$–$C_4$-alkylene)-CO—O-($C_1$–$C_4$-alkylene)-CO—N($R^7$)$R^8$, where $R^6$ is hydrogen, $C_1$–$C_4$-alkyl, $C_1$–$C_4$-alkoxy-$C_1$–$C_4$-alkyl, $C_2$–$C_4$-alkenyl or $C_3$–$C_4$-alkynyl, $R^7$ is hydrogen, $C_1$–$C_4$-alkyl, carboxy-$C_1$–$C_4$-alkyl, ($C_1$–$C_4$-alkoxy)carbonyl-$C_1$–$C_4$-alkyl and $R^8$ is hydrogen or $C_1$–$C_4$-alkyl, or an agriculturally useful salt of a compound I where $R^6$=hydrogen.

2. A substituted 2-phenylpyridine of the formula I as defined in claim 1, where the variables have the following meanings:

n is zero, $R^1$ is chlorine or trifluoromethyl, $R^2$ is chlorine, $R^3$ is hydrogen, fluorine or chlorine, $R^4$ is cyano or chlorine, $R^5$ is —CO—O-($C_1$–$C_4$-alkylene)-CO—$OR^6$, —CO—O-($C_1$–$C_4$-alkylene)-CO—N($R^7$)$R^8$, —O-($C_1$–$C_4$-alkylene)-CO—O($C_1$–$C_4$-alkylene)-CO—$OR^6$ or —O-($C_1$–$C_4$-alkylene)-CO—O-($C_1$–$C_4$-alkylene)-CO—N($R^7$)$R^8$, $R^6$ is $C_1$–$C_4$-alkyl, $C_2$–$C_4$-alkenyl or $C_3$–$C_4$-alkynyl, $R^7$ is $C_1$–$C_4$-alkyl or ($C_1$–$C_4$-alkoxy)carbonyl-$C_1$–$C_4$-alkyl and $R^8$ is hydrogen or $C_1$–$C_4$-alkyl.

3. A herbicidal composition comprising a herbicidally active amount of at least one substituted 2-phenylpyridine of the formula I or of an agriculturally useful salt of I as defined in claim 1 and at least one inert liquid and/or solid carrier and, optionally, at least one surfactant.

4. A composition for the desiccation and/or defoliation of plants comprising such an amount of at least one substituted 2-phenylpyridine of the formula I or of an agriculturally useful salt of I as defined in claim 1 that it acts as a desiccant and/or defoliant, and at least one inert liquid and/or solid carrier and, optionally, at least one surfactant.

5. A process for the preparation of a herbicidally active composition which comprises mixing a herbicidally active amount of at least one substituted 2-phenylpyridine of the formula I or of an agriculturally useful salt of I as defined in claim 1 and at least one inert liquid and/or solid carrier and, optionally, at least one surfactant.

6. A process for the preparation of a composition having a desiccant and/or defoliant action, which comprises mixing such an amount of at least one substituted 2-phenylpyridine of the formula I or of an agriculturally useful salt of I as defined in claim 1 that it acts as a desiccant and/or defoliant, and at least one inert liquid and/or solid carrier and, optionally, at least one surfactant.

7. A method of controlling undesirable vegetation, which comprises applying a herbicidally active amount of at least one substituted 2-phenylpyridine of the formula I or of an agriculturally useful salt of I as defined in claim 1 to on plants, their environment or to seeds.

8. A method for the desiccation and/or defoliation of plants, which comprises applying a desiccation and/or defoliation effective amount of at least one substituted 2-phenylpyridine of the formula I or of an agriculturally useful salt of I as defined in claim 1 to said plants.

9. A method as defined in claim 8, wherein the plants are cotton.

10. A process for the preparation of a substituted 2-phenylpyridine of the formula I as defined in claim 1, which comprises reacting, in the presence of a base, a) an acid chloride of the formula IIa

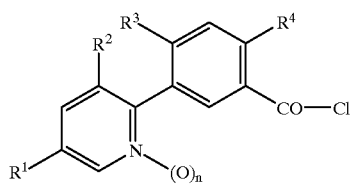

with a hydroxycarboxylic acid or one of its derivatives of the formula IIIa or IIIb HO-($C_1$–$C_4$-alkylene)-CO—$OR^6$   IIIa HO-($C_1$–$C_4$-alkylene)-CO—N($R^7$)$R^8$   IIIb b) an acid chloride of the formula IIb or

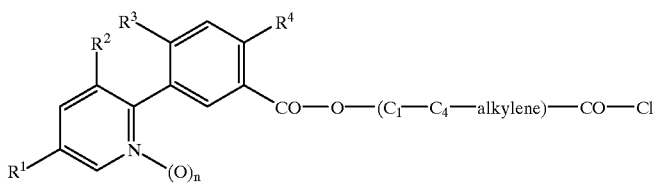

with an alcohol IIIc or amine IIId

HO—R⁶   IIIc

HN(R⁷)R⁸   IIId or c) an acid chloride of the formula IIc

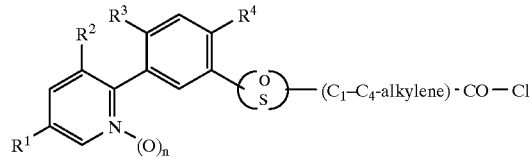

with a hydroxycarboxylic acid or one of its derivatives of the formula IIIa or IIIb.

11. An acid chloride of the formula IIb

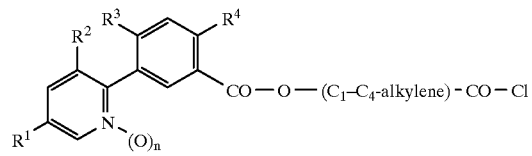

where the variables have the following meanings:

n is 0 or 1;

$R^1$ is halogen or $C_1$–$C_4$-haloalkyl;

$R^2$ and $R^3$ are in each case hydrogen or halogen;

$R^4$ is cyano or halogen.

12. A process for the preparation of an acid chloride of the formula IIb as defined in claim 11, which comprises reacting an acid chloride of the formula IIa with a hydroxycarboxylic acid HO-($C_1$–$C_4$-alkylene)-CO—OH (IV) or with a salt thereof and subsequently chlorinating the process product.

13. A process for the preparation of a substituted 2-phenylpyridine of the formula I as defined in claim 1 where n is 1 and the substituent $R^5$ does not contain a sulfur bridge, which comprises oxidizing the corresponding substituted 2-phenylpyridines where n is zero in an inert solvent or diluent.

14. A process for the preparation of a substituted 2-phenylpyridine of the formula I as defined in claim 1, where $R^5$ is —O-($C_1$–$C_4$-alkylene)-CO—O-($C_1$–$C_4$-alkylene)-CO—OR⁶ or —O-($C_1$–$C_4$-alkylene)-CO—O-($C_1$–$C_4$-alkylene)-CO—N(R⁷)R⁸, which comprises reacting a 3-pyridyiphenol of the formula VI

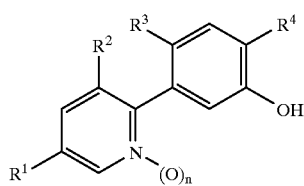

in an inert solvent or diluent, in the presence of a base, with an electrophile of the formula VII L-($C_1$–$C_4$-alkylene)-CO—O-($C_1$–$C_4$-alkylene)-CO—OR⁶   (VII)

or the formula VIII

L-($C_1$–$C_4$-alkylene)-CO—O-($C_1$–$C_4$-alkylene)-CO—N(R⁷)R⁸ (VIII)

where L is in each case chlorine, bromine, iodine, methylsulfonyloxy, trifluoromethylsulfonyloxy, phenylsulfonyloxy or p-toluenesulfonyloxy.

15. A process for the preparation of a substituted 2-phenylpyridine of the formula I as defined in claim 1 where $R^5$ is —S-($C_1$–$C_4$-alkylene)-CO—O-($C_1$–$C_4$-alkylene)-CO—OR⁶ or —S-($C_1$–$C_4$-alkylene)-CO—O-($C_1$–$C_4$-alkylene)-CO—N(R⁷)R⁸, which comprises reacting a 3-pyridylthiophenol of the formula IX

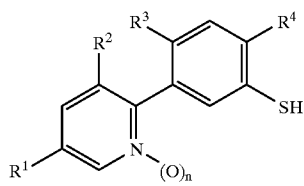

in an inert solvent or diluent, in the presence of a base, with an electrophile of the formula VII L-($C_1$–$C_4$-alkylene)-CO—O-($C_1$–$C_4$-alkylene)-CO—OR⁶   (VII)

or the formula VIII

L-($C_1$–$C_4$-alkylene)-CO—O-($C_1$–$C_4$-alkylene)-CO—N(R⁷)R⁸ (VIII)

where L is in each case chlorine, bromine, iodine, methylsulfonyloxy, trifluoromethylsulfonyloxy, phenylsulfonyloxy or p-toluenesulfonyloxy.

* * * * *

UNITED STATES PATENT AND TRADEMARK OFFICE
CERTIFICATE OF CORRECTION

PATENT NO.: 6,010,980

DATED: January 4, 2000

INVENTOR(S): SCHAEFER et al.

It is certified that error appears in the above-identified patent and that said Letters Patent is hereby corrected as shown below:

Col. 26, claim 7, line 25, delete "on".

Col. 26, claim 9, line 33, "plants are" should be --plant is--.

Col. 27, claim 10, line 17, after "IIId" insert a comma--,--.

Signed and Sealed this

First Day of August, 2000

Attest:

Q. TODD DICKINSON

*Attesting Officer*        *Director of Patents and Trademarks*